(12) United States Patent
Koma et al.

(10) Patent No.: US 10,738,330 B2
(45) Date of Patent: Aug. 11, 2020

(54) APPARATUS FOR PRODUCING ORGANIC SUBSTANCE FROM WASTE AND METHOD FOR PRODUCING ORGANIC SUBSTANCE FROM WASTE

(71) Applicant: SEKISUI CHEMICAL CO., LTD., Osaka (JP)

(72) Inventors: Satoshi Koma, Tokyo (JP); Tetsuya Ishii, Ibaraki (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 0 days.

(21) Appl. No.: 16/236,821

(22) Filed: Dec. 31, 2018

(65) Prior Publication Data

US 2019/0136267 A1 May 9, 2019

Related U.S. Application Data

(62) Division of application No. 15/325,169, filed as application No. PCT/JP2015/071141 on Jul. 24, 2015, now Pat. No. 10,196,655.

(30) Foreign Application Priority Data

Jul. 30, 2014 (JP) ................. 2014-155502

(51) Int. Cl.
*C12M 1/04* (2006.01)
*C12P 7/08* (2006.01)
(Continued)

(52) U.S. Cl.
CPC .................... *C12P 7/08* (2013.01); *B09B 3/00* (2013.01); *B09B 3/0083* (2013.01); *C01B 3/02* (2013.01);
(Continued)

(58) Field of Classification Search
CPC ...................................... C12M 1/04
See application file for complete search history.

(56) References Cited

U.S. PATENT DOCUMENTS

| 6,521,365 B1 | 2/2003 | Song |
| 2008/0166265 A1 | 7/2008 | Day |

(Continued)

FOREIGN PATENT DOCUMENTS

| EP | 2 392 557 | 12/2011 |
| JP | 2001-96260 | 4/2001 |

(Continued)

OTHER PUBLICATIONS

International Search Report dated Oct. 13, 2015 in International (PCT) Application No. PCT/JP2015/071141.
(Continued)

*Primary Examiner* — Rosanne Kosson
(74) *Attorney, Agent, or Firm* — Wenderoth, Lind & Ponack, L.L.P.

(57) ABSTRACT

The present invention provides an apparatus and a method which are suitable for producing an organic substance using a synthesis gas from a waste gasification furnace. The apparatus 1 for producing an organic substance from waste comprises a synthesis gas generation furnace 11 for generating a synthesis gas by partial oxidation of the waste; and an organic substance production unit 12 for producing an organic substance from the synthesis gas. The organic substance production unit 12 further comprises: a synthesis unit 13 for synthesizing an organic substance by subjecting the synthesis gas to catalytic reaction in the presence of a metal catalyst, and a fermenter 14 for producing an organic substance by subjecting the synthesis gas to microbial fermentation.

8 Claims, 1 Drawing Sheet

(51) Int. Cl.
  *B09B 3/00* (2006.01)
  *C08J 11/12* (2006.01)
  *C12P 7/06* (2006.01)
  *C12M 1/00* (2006.01)
  *C01B 3/02* (2006.01)
  *C07C 29/152* (2006.01)
  *C10J 3/82* (2006.01)

(52) U.S. Cl.
  CPC ............ *C07C 29/152* (2013.01); *C08J 11/12* (2013.01); *C10J 3/82* (2013.01); *C12M 21/12* (2013.01); *C12M 43/00* (2013.01); *C12P 7/06* (2013.01); *C08J 2400/30* (2013.01); *C10J 2300/0946* (2013.01); *C10J 2300/0959* (2013.01); *C10J 2300/1846* (2013.01); *Y02E 50/17* (2013.01); *Y02E 50/32* (2013.01); *Y02W 30/703* (2015.05)

(56) References Cited

U.S. PATENT DOCUMENTS

| | | |
|---|---|---|
| 2010/0011778 A1 | 1/2010 | Knight et al. |
| 2010/0298450 A1 | 11/2010 | Datta |
| 2013/0316411 A1 | 11/2013 | Schultz |

FOREIGN PATENT DOCUMENTS

| | | |
|---|---|---|
| JP | 2012-1441 | 1/2012 |
| JP | 2012-149089 | 8/2012 |
| JP | 2012-205530 | 10/2012 |
| JP | 2012-525145 | 10/2012 |
| JP | 2013-199461 | 10/2013 |
| WO | 2005/118826 | 12/2005 |
| WO | 2010/126382 | 11/2010 |
| WO | 2011/087380 | 7/2011 |
| WO | 2012/166267 | 12/2012 |
| WO | 2013/081779 | 6/2013 |
| WO | 2014/046177 | 3/2014 |

OTHER PUBLICATIONS

Extended European Search Report dated Apr. 4, 2018 in European Application No. 15827247.6.
Sebastien Royer et al., "Catalytic Oxidation of Carbon Monoxide over Transition Metal Oxides", Chemcatchem, 3(1): 24-65 (2011).
Notice of Reasons for Rejection dated Dec. 24, 2019 in Japanese Patent Application No. 2016-538324, with English Translation.

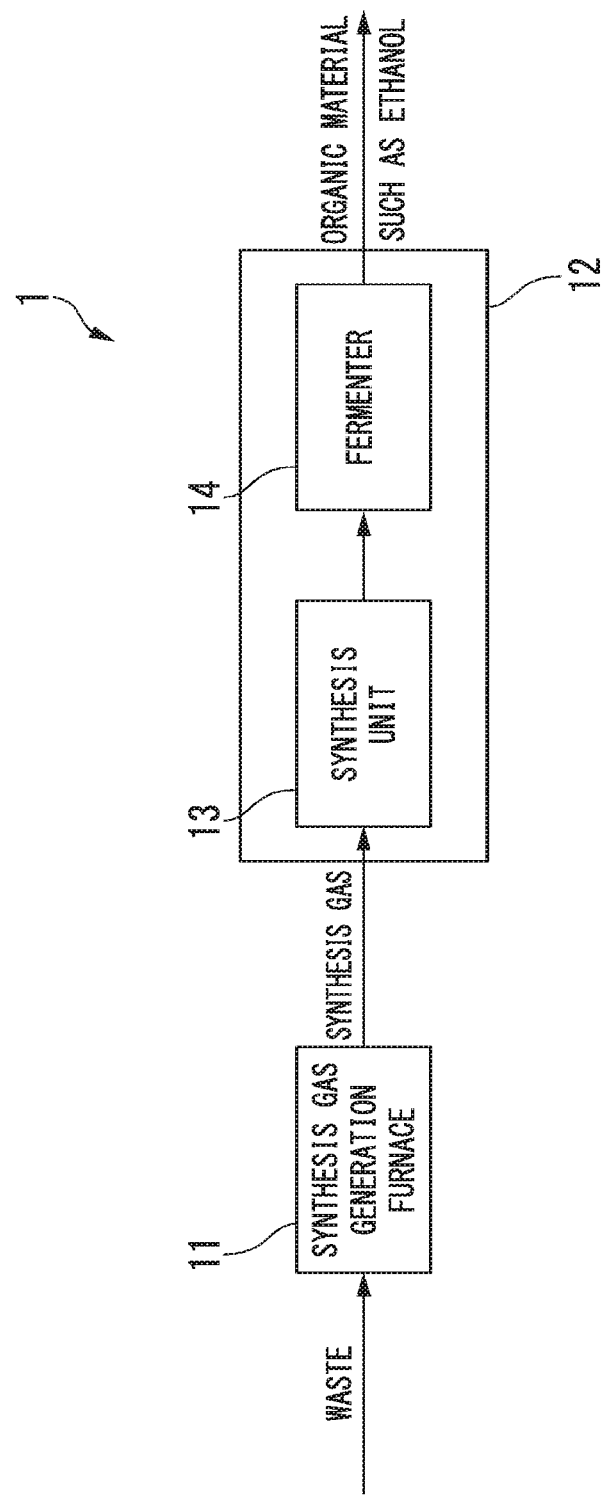

APPARATUS FOR PRODUCING ORGANIC SUBSTANCE FROM WASTE AND METHOD FOR PRODUCING ORGANIC SUBSTANCE FROM WASTE

TECHNICAL FIELD

The present invention relates to an apparatus and a method for producing an organic substance from waste.

DESCRIPTION OF RELATED ART

In recent years, the practical application has been considered with respect to a method for producing a chemical substance such as ethanol by microbial fermentation of a carbon monoxide-containing synthesis gas prepared from an exhaust gas from a steelworks- and the like (see, for example, Patent Document 1).

Conventionally, a method is known in which ethanol is produced by reacting a synthesis gas obtained from biomass in the presence of a catalyst (see Patent Document 2).

DOCUMENTS OF RELATED ART

Patent Document

[Patent Document 1] International Patent Application Publication No. 2011/087380
[Patent Document 2] Japanese Unexamined Patent Application Publication No. 2012-149089

SUMMARY OF THE INVENTION

Problems to be Solved by the Invention

However, so far, a practically applicable apparatus for producing an organic material from waste has not yet been developed, and the fact is that even sufficient research thereon has not been made.

It is a primary object of the present invention to provide an apparatus and a method which can be used for effectively producing an organic substance from a synthesis gas obtained from a waste gasifier furnace.

Means to Solve the Problems

With respect to the apparatus of the present invention for producing an organic substance from waste, the apparatus in a first embodiment thereof comprises: a synthesis gas generation furnace for generating a synthesis gas by partial oxidation of the waste; and an organic substance production unit for producing an organic substance from the synthesis gas. Further, the organic substance production unit comprises: a synthesis unit for synthesizing an organic substance by subjecting the synthesis gas to catalytic reaction in the presence of a metal catalyst, and a fermenter for producing an organic substance by subjecting the synthesis gas to microbial fermentation.

In the apparatus of the first embodiment of the present invention, the fermenter may be connected downstream of the synthesis unit.

In the apparatus of the first embodiment of the present invention, the organic substance may be ethanol.

In the apparatus of the first embodiment of the present invention, the organic substance synthesized in the synthesis unit and the organic substance produced in the fermenter may be different from each other.

With respect to the apparatus of the present invention for producing an organic substance from waste, the apparatus in a second embodiment thereof comprises: a synthesis gas generation furnace for generating a synthesis gas by partial oxidation of the waste; and an organic substance production unit for producing an organic substance from the synthesis gas. Further, the organic substance production unit comprises: a synthesis unit for synthesizing a first organic substance by subjecting the synthesis gas to catalytic reaction in the presence of a metal catalyst, and a fermenter for producing a second organic substance by subjecting the first organic substance to microbial fermentation, the fermenter being connected in series to the synthesis unit.

In the apparatus of the second embodiment of the present invention, the first organic substance may be at least one substance selected from the group consisting of alcohols having 6 or less carbon atoms, aldehydes having 6 or less carbon atoms, and carboxylic acids having 6 or less carbon atoms, and the second organic substance may be at least one substance selected from the group consisting of alcohols, organic acids, fatty acids, fats and oils, ketones, dienes, biomass and saccharides.

DETAILED DESCRIPTION OF THE INVENTION

With respect to the method of the present invention for producing an organic substance from waste, the method in a first embodiment thereof comprises: a synthesis gas-generating step for generating a synthesis gas by partial oxidation of waste; and an organic substance-producing step for producing an organic substance from the synthesis gas. Further, the organic substance-producing step comprises: a synthesizing step for synthesizing an organic substance by subjecting the synthesis gas to catalytic reaction in the presence of a metal catalyst in a synthesis unit; and a fermentation step for producing an organic substance by subjecting the synthesis gas to microbial fermentation in a fermenter.

In the method of the first embodiment of the present invention, the fermentation step may be performed after the synthesizing step.

In the method of the first embodiment of the present invention, the organic substance may be ethanol.

In the method of the first embodiment of the present invention, the organic substance synthesized in the synthesizing step and the organic substance produced in the fermentation step may be different from each other.

With respect to the method of the present invention for producing an organic substance from waste, the method in a second embodiment thereof comprises: a synthesis gas-generating step for generating a synthesis gas by partial oxidation of waste; and an organic substance-producing step for producing an organic substance from the synthesis gas. Further, the organic substance-producing step comprises: a synthesizing step for synthesizing a first organic substance by subjecting the synthesis gas to catalytic reaction in the presence of a metal catalyst in a synthesis unit; and a fermentation step for producing a second organic substance by subjecting the first organic substance to microbial fermentation in a fermenter which is connected in series to the synthesis unit.

In the method of the present invention of the second embodiment, the first organic substance may be at least one substance selected from the group consisting of alcohols having 6 or less carbon atoms, aldehydes having 6 or less carbon atoms, and carboxylic acids having 6 or less carbon atoms, and the second organic substance may be at least one substance selected from the group consisting of alcohols, organic acids, fatty acids, fats and oils, ketones, dienes, biomass and saccharides.

Effect of the Invention

As described above, the present invention can provide an apparatus and a method which can be used for effectively producing an organic substance from a synthesis gas obtained from a waste gasifier furnace.

BRIEF DESCRIPTION OF THE DRAWINGS

FIG. 1 is a schematic view of the apparatus for producing an organic substance from waste according to one embodiment of the present invention.

DESCRIPTION OF THE EMBODIMENTS

Hereinbelow, the present invention will be described in detail with reference to preferred embodiments of the present invention. However, these embodiments are only examples. The present invention is in no way limited by these embodiments.

First Embodiment

FIG. 1 is a schematic view of the apparatus for producing an organic substance from waste. The apparatus 1 shown in FIG. 1 is an apparatus for producing an organic substance from waste including waste plastic and the like. For example, the organic substance to be produced may be alcohols, organic acids, fatty acids, fats and oils, ketones, biomass, saccharides and the like. More specific examples of the organic substance include ethanol, acetic acid, butanediol and the like. Hereinbelow, the present invention will be described in detail with reference to an embodiment in which ethanol is produced.

The obtained organic substance may be used for any purposes without any limitation. For example, the obtained organic substance can be used not only as a material for plastic, resin and the like, but also as fuel.

The apparatus 1 has a synthesis gas generation furnace 11. A waste containing organic substances such as plastic, resin and the like is fed into the synthesis gas generation furnace 11. In the synthesis gas generation furnace 11, the waste is partially oxidized so as to generate a synthesis gas. The obtained synthesis gas contains carbon monoxide and hydrogen gas. A synthesis gas generated by partial oxidization of waste generally contains carbon monoxide and hydrogen at a molar ratio of 1:1.5 to 1.5:1.

The synthesis gas generation furnace 11 is connected to an organic substance production unit 12. The synthesis gas obtained from the synthesis gas generation furnace 11 is fed into the organic substance production unit 12. Between the synthesis gas generation furnace 11 and the organic substance production unit 12, there may be provided a synthesis gas purifier, a synthesis gas reformer, a carbon dioxide separator, and the like.

The organic substance production unit 12 has a synthesis unit 13 and a fermenter 14. The synthesis unit 13 is connected to the synthesis gas generation furnace 11. A synthesis gas obtained from the synthesis gas generation furnace 11 is fed into the synthesis unit 13. The synthesis unit 13 contains a metal catalyst therein. In the synthesis unit 13, an organic substance is synthesized by subjecting a synthesis gas to catalytic reaction in the presence of a metal catalyst.

As an example of the metal catalyst preferably used in the catalytic reaction in the present invention, a four-way catalyst composed of rhodium, manganese, lithium, magnesium and the like can be mentioned. In the catalytic reaction in the synthesis unit 13, 2 mol of hydrogen is consumed per 1 mol of carbon monoxide.

The fermenter 14 is connected to the synthesis unit 13. Namely, the fermenter 14 and the synthesis unit 13 are connected in series to each other. A gas exhausted from the synthesis unit 13 is fed into the fermenter 14. In the synthesis unit 13, hydrogen is consumed more than carbon monoxide, so that the exhausted gas from the synthesis unit 13 contains at least carbon monoxide.

The fermenter 14 contains microorganisms. The microorganisms in the fermenter 14 cause the fermentation of the exhausted gas from the synthesis unit 13 to thereby produce ethanol. As specific examples of the microorganisms preferably used for producing ethanol in the fermenter 14, anaerobic carboxydotrophic bacteria such as *Clostridium* genus and the like can be mentioned. In the microbial fermentation in the fermenter 14, ethanol is synthesized from carbon monoxide even without separately supplying hydrogen needed for the microbial fermentation, because the necessary hydrogen is obtained from water present in the system.

As mentioned above, a synthesis gas generated by partial oxidization of waste generally contains carbon monoxide and hydrogen at a molar ratio of 1.5:1 to 1:1.5. In the catalytic reaction in the synthesis unit 13, 2 mol of hydrogen is consumed per 1 mol of carbon monoxide. Therefore, for example, in the case where only the synthesis unit 13 is provided, carbon monoxide contained in the obtained synthesis gas is not completely consumed.

However, in the apparatus 1 of the present invention, the synthesis unit 13 (wherein a metal catalyst is used) and the fermenter 14 are connected to each other in series. Therefore, excessive carbon monoxide in the synthesis unit 13 is consumed in the fermenter 14 to form ethanol. Accordingly, by the use of the apparatus 1 of the present invention, the utilization rate of carbon monoxide contained in the synthesis gas can be improved. As a result, the apparatus 1 of the present invention enables production of ethanol with high efficiency.

In this embodiment of the present invention, the fermenter 14 is connected downstream of the synthesis unit 13. The fermenter 14 is more likely to cause a side reaction than the synthesis unit 13. For this reason, in the fermenter 14, by-products are formed in greater amounts than in the synthesis unit 13. Accordingly, in the organic substance production unit 12, the synthesis unit 13 with less formation of by-products is preferably disposed upstream, while the fermenter 14 with greater formation of by-products is preferably disposed downstream. With such a configuration, the catalyst deterioration in the synthesis unit 13, which is caused by the by-products formed in the fermenter 14, can be suppressed. However, the present invention is in no way limited to such a configuration. The synthesis unit 13 may be connected downstream of the fermenter 14.

Hereinbelow, the present invention will be described in detail with reference to further preferred embodiments of the present invention. In the following descriptions, components having substantially the same functions as those in the first embodiment are denoted with the same reference numerals, and the descriptions thereof are omitted. In the following embodiment, reference is also made to FIG. 1 as in the first embodiment.

Second Embodiment

In the first embodiment, explanation is made as to the embodiment in which the organic substance synthesized in the synthesis unit 13 and the organic substance produced in the fermenter 14 are the same. However, the present invention is in no way limited to the above embodiment.

In the present invention, the organic substance synthesized in the synthesis unit 13 and the organic substance produced in the fermenter 14 may be different from each other. In such a case, a plurality of organic substances can be produced.

For example, the organic substance synthesized in the synthesis unit 13 may be ethanol, while the organic substance produced in the fermenter 14 may be acetic acid. In another example, the organic substance synthesized in the synthesis unit 13 may be acetaldehyde, while the organic substance produced in the fermenter 14 may be ethanol.

Further, in the first embodiment, explanation is made as to an example where the synthesis unit 13 and the fermenter 14 are connected in series to each other. However, in the second embodiment, the synthesis unit 13 and the fermenter 14 are not necessarily required to be connected in series to each other. For example, the synthesis unit 13 and the fermenter 14 may be connected in parallel to each other. In another example, the synthesis unit 13 may be connected downstream of the fermenter 14. In the second embodiment, the manner of connection between the synthesis unit 13 and the fermenter 14 can be determined appropriately, for example, in accordance with the kinds of the organic substances to be synthesized in the synthesis unit 13 and produced in the fermenter 14.

Third Embodiment

In the first and second embodiments, explanation is made as to examples where each of the synthesis unit 13 and the fermenter 14 consumes a synthesis gas as the raw material. However, the present invention is in no way limited to the above embodiment.

For example, in this third embodiment, the synthesis unit 13 synthesizes a first organic substance. Then, the fermenter 14 produces a second organic substance by subjecting the first organic substance to microbial fermentation. By this configuration, it is possible to produce an organic substance that is difficult to produce directly by microbial fermentation of a synthesis gas. Further, by subjecting not all but a part of the first organic substances to microbial fermentation in the fermenter 14, it is possible to produce both of the first and the second organic substances.

The kinds of the first and the second organic substances are not particularly limited. For example, the first organic substance may be at least one substance selected from the group consisting of alcohols having 6 or less carbon atoms, aldehydes having 6 or less carbon atoms, and carboxylic acids having 6 or less carbon atoms, and the second organic substance may be at least one substance selected from the group consisting of alcohols, organic acids, fatty acids, fats and oils, ketones, dienes, biomass and saccharides.

In the third embodiment, explanation is made as to an example where the fermenter 14 is connected downstream of the synthesis unit 13. However, the present invention is in no way limited to such a configuration. For example, the synthesis unit 13 may be connected downstream of the fermenter 14. In such a case, using one organic substance produced in the fermenter 14 as a raw material, another organic substance is synthesized in the synthesis unit 13.

DESCRIPTION OF THE REFERENCE SIGNS

1: Apparatus
11: Synthesis gas generation furnace
12: Organic substance production unit
13: Synthesis unit
14: Fermenter

What is claimed is:

1. An apparatus for producing an organic substance from waste, comprising:
    a) a synthesis gas generation furnace for generating a synthesis gas by partial oxidation of the waste; and
    b) an organic substance production unit for producing an organic substance from the synthesis gas, the organic substance production unit further comprising:
        i) a synthesis unit for synthesizing an organic substance by subjecting the synthesis gas to catalytic reaction in the presence of a metal catalyst, and
        ii) a fermenter for producing an organic substance by subjecting the synthesis gas to microbial fermentation.

2. The apparatus according to claim 1, wherein the fermenter is connected downstream of the synthesis unit.

3. The apparatus according to claim 1, wherein the organic substance is ethanol.

4. The apparatus according to claim 1, wherein the organic substance synthesized in the synthesis unit and the organic substance produced in the fermenter are different from each other.

5. An apparatus for producing an organic substance from waste, comprising:
    a) a synthesis gas generation furnace for generating a synthesis gas by partial oxidation of the waste; and
    b) an organic substance production unit for producing an organic substance from the synthesis gas, the organic substance production unit further comprising:
        i) a synthesis unit for synthesizing a first organic substance by subjecting the synthesis gas to catalytic reaction in the presence of a metal catalyst, and
        ii) a fermenter for producing a second organic substance by subjecting the first organic substance to microbial fermentation, the fermenter being connected in series to the synthesis unit.

6. The apparatus according to claim 5, wherein:
    the first organic substance is at least one substance selected from the group consisting of alcohols having 6 or less carbon atoms, aldehydes having 6 or less carbon atoms, and carboxylic acids having 6 or less carbon atoms, and
    the second organic substance is at least one substance selected from the group consisting of alcohols, organic acids, fatty acids, fats and oils, ketones, dienes, biomass and saccharides.

7. The apparatus according to claim 2, wherein the organic substance is ethanol.

8. The apparatus according to claim 2, wherein the organic substance synthesized in the synthesis unit and the organic substance produced in the fermenter are different from each other.

* * * * *